(12) United States Patent
Ross

(10) Patent No.: US 8,696,637 B2
(45) Date of Patent: Apr. 15, 2014

(54) TRANSDERMAL PATCH CONTAINING MICRONEEDLES

(75) Inventor: Russell F. Ross, Atlanta, GA (US)

(73) Assignee: Kimberly-Clark Worldwide, Neenah, WI (US)

(*) Notice: Subject to any disclaimer, the term of this patent is extended or adjusted under 35 U.S.C. 154(b) by 457 days.

(21) Appl. No.: 13/036,096

(22) Filed: Feb. 28, 2011

(65) Prior Publication Data
US 2012/0220980 A1    Aug. 30, 2012

(51) Int. Cl.
| A61M 5/00 | (2006.01) |
| A61B 17/20 | (2006.01) |
| A61M 37/00 | (2006.01) |
| A61M 5/32 | (2006.01) |

(52) U.S. Cl.
USPC .............. 604/173; 604/46; 604/47; 604/244; 604/272

(58) Field of Classification Search
USPC ......... 604/46, 47, 73, 80, 173, 191, 244, 272, 604/22, 48, 93.01, 264; 606/185, 186
See application file for complete search history.

(56) References Cited

U.S. PATENT DOCUMENTS

| 3,797,494 A | | 3/1974 | Zaffaroni | |
| 3,964,482 A | * | 6/1976 | Gerstel et al. ............... | 604/890.1 |
| 4,031,894 A | | 6/1977 | Urquhart et al. | |
| 4,167,179 A | * | 9/1979 | Kirsch .............................. | 600/7 |
| 4,201,211 A | | 5/1980 | Chandrasekaran et al. | |
| 4,379,454 A | | 4/1983 | Campbell et al. | |
| 4,436,741 A | | 3/1984 | Urquhart et al. | |

(Continued)

FOREIGN PATENT DOCUMENTS

| WO | WO 2011/070457 | 6/2011 |
| WO | WO 2011/135530 | 11/2011 |

(Continued)

OTHER PUBLICATIONS

Search Report and Written Opinion for PCT/IB2012/050203 dated Aug. 30, 2012, 12 pages.

(Continued)

Primary Examiner — Kevin C. Sirmons
Assistant Examiner — Shefali Patel
(74) Attorney, Agent, or Firm — Dority & Manning, PA

(57) ABSTRACT

A transdermal patch that can easily deliver a controlled volume of a fluidic drug compound to skin is provided. More particularly, the patch contains a microneedle assembly that is configured to be placed in fluid communication with a drug delivery assembly. The microneedle assembly contains a support and a plurality of microneedles that extend outwardly from the support. The microneedles are formed with one or more channels of a certain dimension such that passive capillary flow drives a flow of the drug compound. The drug delivery assembly contains a reservoir for the drug compound that is in fluid communication with a rate control membrane that helps control a flow rate of the drug compound by modulating a pressure of the drug compound, downstream from the reservoir. A release member is also positioned adjacent to the microneedle and drug delivery assemblies. Prior to use, the release member acts as a barrier to the flow of the drug compound and thus inhibits premature leakage. In this manner, the patch can initially be provided in an "inactive" configuration in which the drug compound is securely retained. When it is desired to release the drug compound, the patch can simply be activated by at least partially separating the release member from the drug delivery and microneedle assemblies.

17 Claims, 9 Drawing Sheets

(56) References Cited

U.S. PATENT DOCUMENTS

| | | |
|---|---|---|
| 4,588,580 A | 5/1986 | Gale et al. |
| 4,615,699 A | 10/1986 | Gale et al. |
| 4,661,105 A | 4/1987 | Gale |
| 4,681,584 A | 7/1987 | Gale et al. |
| 4,698,062 A | 10/1987 | Gale et al. |
| 4,725,272 A | 2/1988 | Gale |
| 4,832,953 A | 5/1989 | Campbell et al. |
| 4,880,633 A | 11/1989 | Loper et al. |
| 4,908,027 A | 3/1990 | Enscore et al. |
| 5,004,610 A | 4/1991 | Osborne et al. |
| 5,310,559 A | 5/1994 | Shah et al. |
| 5,342,623 A | 8/1994 | Enscore et al. |
| 5,344,656 A | 9/1994 | Enscore et al. |
| 5,364,630 A | 11/1994 | Osborne et al. |
| 6,132,755 A | 10/2000 | Eicher et al. |
| 6,375,978 B1 | 4/2002 | Kleiner et al. |
| 6,569,143 B2 | 5/2003 | Alchas et al. |
| 6,591,124 B2 | 7/2003 | Sherman et al. |
| 6,611,707 B1 | 8/2003 | Prausnitz et al. |
| 6,656,147 B1 | 12/2003 | Gertsek et al. |
| 6,881,203 B2 | 4/2005 | Delmore et al. |
| 6,908,453 B2 | 6/2005 | Fleming et al. |
| 6,980,855 B2 | 12/2005 | Cho |
| 7,048,723 B1 | 5/2006 | Frazier et al. |
| 7,066,922 B2 | 6/2006 | Angel et al. |
| 7,108,681 B2 | 9/2006 | Gartstein et al. |
| 7,131,987 B2 | 11/2006 | Sherman et al. |
| 7,226,439 B2 | 6/2007 | Prausnitz et al. |
| 7,250,037 B2 | 7/2007 | Shermer et al. |
| 7,285,113 B2 | 10/2007 | Yeshurun |
| 7,315,758 B2 | 1/2008 | Kwiatkowski et al. |
| 7,364,568 B2 | 4/2008 | Angel et al. |
| 7,410,476 B2 | 8/2008 | Wilkinson et al. |
| 7,416,541 B2 | 8/2008 | Yuzhakov et al. |
| 7,429,258 B2 | 9/2008 | Angel et al. |
| 7,537,590 B2 | 5/2009 | Santini, Jr. et al. |
| 7,578,954 B2 | 8/2009 | Gartstein et al. |
| 7,582,069 B2 | 9/2009 | Laurent et al. |
| 7,588,552 B2 | 9/2009 | Yeshurun et al. |
| 7,611,481 B2 | 11/2009 | Cleary et al. |
| 7,627,938 B2 | 12/2009 | Kim et al. |
| 7,651,475 B2 | 1/2010 | Angel et al. |
| 7,658,728 B2 | 2/2010 | Yuzhakov |
| 7,753,888 B2 | 7/2010 | Murkerjee et al. |
| 7,785,301 B2 | 8/2010 | Yuzhakov |
| 7,846,488 B2 | 12/2010 | Johnson et al. |
| 7,901,387 B2 | 3/2011 | Stemme et al. |
| 7,914,480 B2 | 3/2011 | Cleary et al. |
| 7,914,813 B2 | 3/2011 | Adachi et al. |
| 7,918,814 B2 | 4/2011 | Prausnitz et al. |
| 8,088,321 B2 | 1/2012 | Ferguson et al. |
| 2002/0183688 A1 | 12/2002 | Lastovich et al. |
| 2003/0050602 A1 | 3/2003 | Pettis et al. |
| 2003/0187394 A1 | 10/2003 | Wilkinson et al. |
| 2004/0087992 A1 | 5/2004 | Gartstein et al. |
| 2004/0106904 A1 | 6/2004 | Gonnelli et al. |
| 2005/0143713 A1 | 6/2005 | Delmore et al. |
| 2005/0177106 A1* | 8/2005 | Naimark et al. ............. 604/104 |
| 2005/0178760 A1 | 8/2005 | Chang et al. |
| 2005/0181033 A1* | 8/2005 | Dekker et al. ............. 424/449 |
| 2005/0187521 A1 | 8/2005 | Fleming et al. |
| 2007/0250018 A1 | 10/2007 | Adachi et al. |
| 2007/0276318 A1 | 11/2007 | Henley |
| 2008/0015494 A1 | 1/2008 | Santini, Jr. et al. |
| 2008/0091226 A1 | 4/2008 | Yeshurun et al. |
| 2008/0195035 A1 | 8/2008 | Frederickson et al. |
| 2008/0269685 A1 | 10/2008 | Singh et al. |
| 2009/0030365 A1 | 1/2009 | Tokumoto et al. |
| 2009/0069788 A1 | 3/2009 | Yeshurun et al. |
| 2009/0093776 A1 | 4/2009 | Yue et al. |
| 2009/0099427 A1 | 4/2009 | Jina et al. |
| 2009/0099502 A1 | 4/2009 | Tokumoto et al. |
| 2009/0118662 A1 | 5/2009 | Schnall |
| 2009/0137926 A1 | 5/2009 | Srinivasan et al. |
| 2009/0198189 A1 | 8/2009 | Simons et al. |
| 2010/0121307 A1 | 5/2010 | Lockard et al. |
| 2010/0256568 A1 | 10/2010 | Frederickson et al. |
| 2010/0274203 A1 | 10/2010 | Lee et al. |
| 2011/0021996 A1 | 1/2011 | Lee et al. |
| 2011/0046557 A1 | 2/2011 | Lee et al. |
| 2011/0059150 A1 | 3/2011 | Kendall et al. |
| 2011/0270221 A1 | 11/2011 | Ross |

FOREIGN PATENT DOCUMENTS

| | | |
|---|---|---|
| WO | WO 2011/135531 | 11/2011 |
| WO | WO 2011/135532 | 11/2011 |
| WO | WO 2012/020332 | 2/2012 |
| WO | WO 2012/046149 | 4/2012 |

OTHER PUBLICATIONS

Kumar, et al., "Transdermal Drug Delivery System: An Overview", *International Journal of Pharmaceutical Sciences Review and Research*, vol. 3, Issue 2, Jul.-Aug. 2010, Article 009.

* cited by examiner

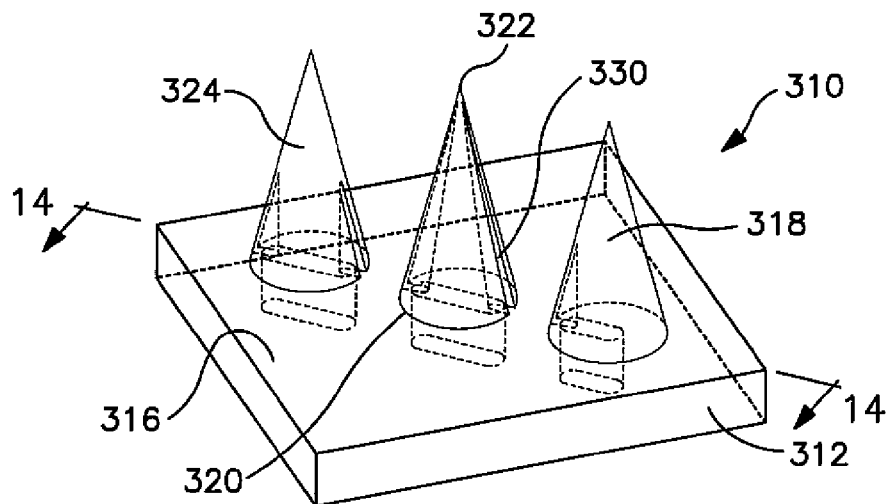
FIG. 13
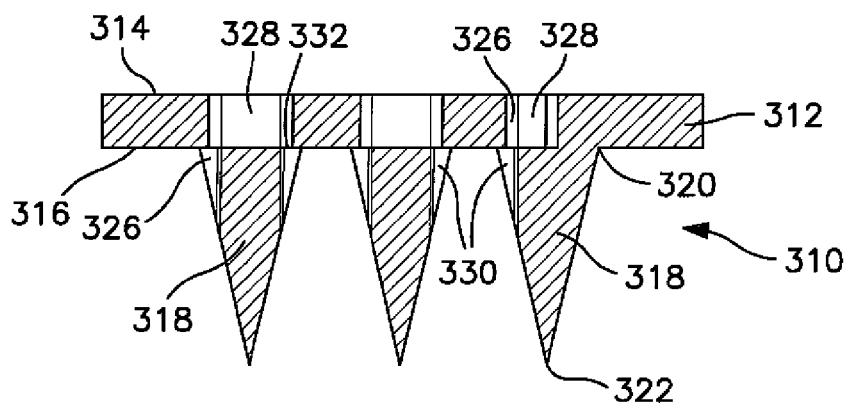
FIG. 14
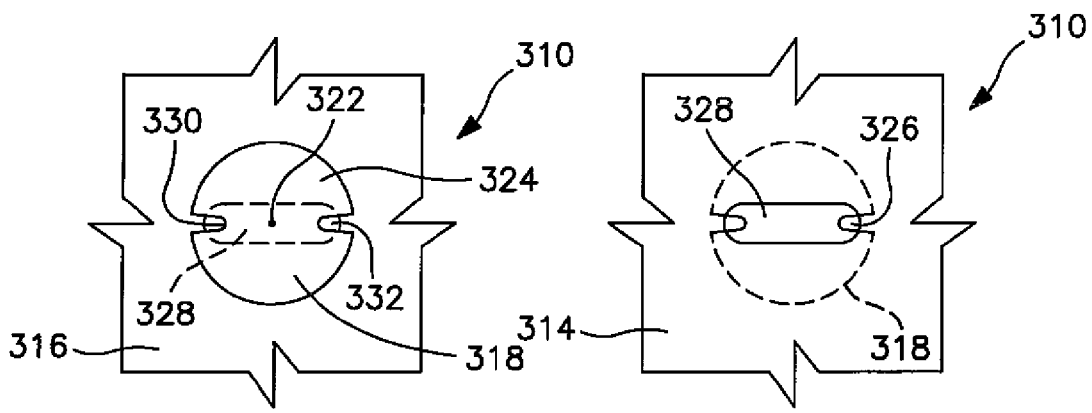
FIG. 15   FIG. 16

TRANSDERMAL PATCH CONTAINING MICRONEEDLES

BACKGROUND OF THE INVENTION

The delivery of drugs to a patient is conventionally performed in a number of different ways. For example, intravenous delivery is by injection directly into a blood vessel; intraperitoneal delivery is by injection into the peritoneum; subcutaneous delivery is under the skin; intramuscular delivery is into a muscle; and oral delivery is through the mouth. One of the easiest methods for drug delivery, and for collection of body fluids, is through the skin. Skin is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue that extends around 10-20 microns from the skin surface and has no blood supply. Because of the density of this layer of cells, moving compounds across the skin, either into or out of the body, can be very difficult.

Current techniques for delivering local pharmaceuticals through the skin include methods that use needles or other skin piercing devices and methods that do not use such devices. Those methods that do not use needles typically involve: (a) topical applications, (b) iontophoresis, (c) electroporation, (d) laser perforation or alteration, (e) carriers or vehicles, which are compounds that modify the chemical properties of either the stratum corneum and/or the pharmaceutical, (f) physical pretreatment of the skin, such as abrasion of the stratum corneum (e.g., repeatedly applying and removing adhesive tape), and (g) sonophoresis, which involves modifying the barrier function of stratum corneum by ultrasound. Invasive procedures, such as use of needles or lances, can effectively overcome the barrier function of the stratum corneum. However, these methods suffer from several major disadvantages, including pain, local skin damage, bleeding, risk of infection at the injection site, and creation of contaminated needles or lances. These methods also usually require a trained administrator and are not suitable for repeated, long-term, or controlled use. Additionally, drug delivery through the skin has been relatively imprecise in both location and dosage of the pharmaceutical. Some of the problems include movement of the patient during administration, delivery of incomplete dosages, difficulties in administering more than one pharmaceutical at the same time, and difficulties in delivering a pharmaceutical to the appropriate part of the skin. Drugs have traditionally been diluted to enable handling of the proper dosages. This dilution step can cause storage as well as delivery problems. Thus, it would be advantageous to be able to use small, precise volumes of pharmaceuticals for quick, as well as long-term, delivery through the skin.

Microneedles have been proposed for this purpose. The microneedles typically have a hollow shaft, similar to larger conventional medical needles, so that drug compounds may be delivered through the hollow shaft. Various mechanisms have been employed to initiate the flow of the drug compound through such devices. U.S. Pat. No. 6,611,707 to Prausnitz et al., for example, describes a device having one or more drug reservoirs positioned over a housing that includes an array of hollow microneedles. A drug is delivered from the reservoir by applying a physical force, such as by pressing the top of the reservoir, to cause the drug to flow out through the microneedles. Unfortunately, due to their very small size, the hollow shafts of microneedles can break off when the physical force is applied. Further, the delivery of a drug compound that is initiated by such a physical force is sometimes too fast for achieving a controlled flow rate. U.S. Pat. No. 7,651,475 to Angel, et al. describes one attempt to overcome these problems by employing an actuator that pumps the drug compound between the reservoir and the body through the needles. While potentially helping to achieve a controlled flow rate, the use of such actuators (pumps) to induce flow is nevertheless cost prohibitive and overly complex, particularly when the product is intended for use by a person other than a medical professional.

As such, a need currently exists for a transdermal microneedle device that can easily deliver a drug compound without the need for active displacement mechanisms, such as pumps.

SUMMARY OF THE INVENTION

In accordance with one embodiment of the present invention, a transdermal patch is disclosed that comprises a drug delivery assembly and a microneedle assembly. The drug delivery assembly comprises a reservoir for holding a drug compound and a rate control membrane that is in fluid communication with the reservoir. The microneedle assembly comprises a support having a first surface and a second surface, wherein an aperture, extends between the first surface of the support and the second surface of the support. The microneedle assembly further comprises a plurality of microneedles that extend outwardly from the second surface of the support. At least one of the microneedles contains a channel that is in fluid communication with the aperture of the support and has a cross-sectional dimension ranging from about 1 micrometer to about 100 micrometers. A release member that is generally impermeable to the drug compound is positioned adjacent to the rate control membrane of the drug delivery assembly and the first surface of the support of the microneedle assembly. The release member is configured to be at least partially separated from the rate control membrane of the drug delivery assembly and the support of the microneedle assembly when the patch is an active configuration.

In accordance with another embodiment of the present invention, a method for transdermally delivering a drug compound is disclosed. The method comprises placing a patch adjacent to skin, the patch comprising a drug delivery assembly that comprises a reservoir that holds a drug compound and a rate control membrane; a microneedle assembly that comprises a support that defines an aperture, the microneedle assembly comprising a plurality of microneedles that extend outwardly from the support and contain a channel in fluid communication with the aperture of the support; and a release member that is generally impermeable to the drug compound and positioned adjacent to the rate control membrane and the support. The patch is activated to release the drug compound from the reservoir, through the rate control membrane and aperture of the support, and into the channel of the microneedles. The activation of the patch includes at least partially separating the release member from the rate control membrane and the support.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 13 is a perspective view of a microneedle assembly that may be employed in one embodiment of the transdermal patch of the present invention;

FIG. 14 is a cross-sectional view of the microneedle assembly of FIG. 13, taken along lines 14-14;

FIG. 15 is a top view of a microneedle assembly that may be employed in one embodiment of the transdermal patch of the present invention;

FIG. 16 is a bottom view of a microneedle assembly that may be employed in one embodiment of the transdermal patch of the present invention;

Figure 1:
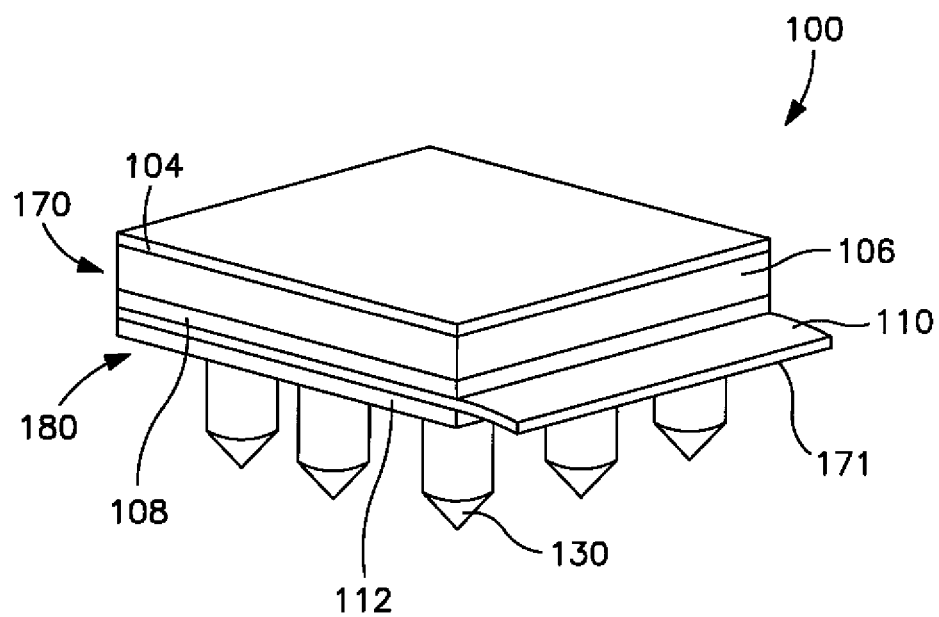
FIG. 1 is a perspective view of one embodiment of the transdermal patch of the present invention prior to delivery of a drug compound.

Repeat use of reference characters in the present specification and figures is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a transdermal patch that can easily deliver a controlled volume of a fluidic drug compound to the skin. More particularly, the patch contains a microneedle assembly that is configured to be placed in fluid communication with a drug delivery assembly. The microneedle assembly contains a support and a plurality of microneedles that extend outwardly from the support. The microneedles are formed with one or more channels of a certain dimension such that passive capillary flow drives the flow of the drug compound. The drug delivery system contains a reservoir for the drug compound that is in fluid communication with a rate control membrane that helps control the flow rate of the drug compound by modulating its pressure downstream from the reservoir. A release member is also positioned adjacent to the microneedle and drug delivery assemblies. Prior to use, the release member acts as a barrier to the flow of the drug compound and thus inhibits premature leakage. In this manner, the patch can initially be provided in an "inactive" configuration in which the drug compound is securely retained. When it is desired to release the drug compound, the patch can simply be activated by at least partially separating (e.g., detaching, rupturing, etc.) the release member from the drug delivery assembly and the microneedle assembly. Notably, through the synergistic combination of features noted above, the flow of the drug compound can be induced "passively"—i.e., without the need for conventional active displacement mechanisms, such as liquid pumps, actuators, plungers, finger pressure, etc. This allows the patch to be placed on the skin before activation, thereby limiting potential spillage of the drug compound. The passive delivery of the drug compound is also simple and easy to use, which enables it to be used by a wide variety of consumers, not just medical professionals. Various embodiments of the present invention will now be described more detail below.

1. Drug Delivery Assembly

A. Reservoir

As indicated above, the drug delivery assembly of the transdermal patch contains a reservoir that can initially retain a drug compound. The term "reservoir" generally refers to a designated area or chamber configured to retain a fluidic drug compound. The reservoir may be an open volume space, gel, solid structure, etc. Nevertheless, in most embodiments, the reservoir is a solid matrix through which the drug compound is capable of flowing. The selection of the desired materials for the matrix typically depends on the solubility and diffusivity of the target drug compound and the time during which release is sought. In one embodiment, for example, the solid matrix is generally impermeable to the compound, and the material used to form the matrix is selected so that the drug compound is able to diffuse therethrough. In other embodiments, however, the solid matrix may be permeable or semi-permeable to the drug compound so that it can simply flow through its pores. Examples of such solid matrices include porous fiber webs (e.g., woven or nonwoven), apertured films, foams, sponges, etc. Regardless of its particular form, polymeric materials are often used to form the solid matrix, such as silicones, acrylic resins, acetate copolymers (e.g., ethylene vinyl acetate), plasticized polyvinyl acetate/polyvinyl chloride resins, plasticized hydrolyzed polyvinyl alcohol, rubber-based adhesives (e.g., polyisobutylenes extended with a solvent such as mineral oil), plasticized polyvinyl chloride, polyethylene glycols and polypropylene glycols of varying molecular weights, cellulose esters, polyolefins; etc.

There is no particular limitation to the drug compounds that may be retained within the reservoir and employed in the patch of the present invention. Suitable compounds may include, for instance, proteinaceous compounds, such as insulin, immunoglobulins (e.g., IgG, IgM, IgA, IgE), TNF-α, antiviral medications, etc.; polynucleotide agents, such as plasmids, siRNA, RNAi, nucleoside anticancer drugs, vaccines, etc.; small molecule agents, such as alkaloids, glycosides, phenols, etc.; anti-infection agents, hormones, drugs regulating cardiac action or blood flow, pain control; and so forth. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, nonsteroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143, which is incorporated herein by reference. Vaccine formulations may include an antigen or antigenic composition capable of eliciting an immune response against a human pathogen or from other viral pathogens.

Due to its controlled capillary flow, the patch of the present invention may be particularly beneficial in delivering high molecular weight drug compounds that were previously difficult to deliver via transdermal delivery. The term "high molecular weight" generally refers to compounds having a molecular weight of about 1 kiliDalton ("kDa") or more, in some embodiments about 10 kDa or more, in some embodiments about 20 kDa to about 250 kDa, and in some embodiments, from about greater than about 40 kDa to about 150 kDa. Examples of such high molecular weight compounds include protein therapeutics, which refers to any biologically active proteinaceous compound including, without limitation, natural, synthetic, and recombinant compounds, fusion proteins, chimeras, and so forth, as well as compounds including the 20 standard amino acids and/or synthetic amino acids. In one particular embodiment, the patch may be utilized in treatment of a chronic condition, such as rheumatoid arthritis ("RA"), to deliver a steady flow a drug to a subject in need thereof. RA drug compounds may include symptom suppression compounds, such as analgesics and anti-inflammatory drugs including both steroidal and non-steroidal anti-inflammatory drugs (NSAID), as well as disease-modifying antirheumatic drugs ("DMARD"). The patch can include and deliver symptom suppression compounds, such as analgesics and anti-inflammatory drugs, as well as DMARD compounds, including biological DMARDs. Through utilization of the transdermal patch of the present invention, RA drugs can be delivered at a steady concentration over a sustained period. The patch can prevent the initial burst of concentration common when utilizing previously known methods for delivery of RA drugs, including oral delivery and injection.

RA drugs that may be incorporated in the patch can include, without limitation, one or more analgesics, anti-inflammatories, DMARDs, herbal-based drugs, and combinations thereof. Specific compounds can, of course, fall under one or more of the general categories described herein. For instance, many compounds function as both an analgesic and an anti-inflammatory; herbal-based drugs can likewise function as a DMARD as well as an anti-inflammatory. Moreover, multiple compounds that can fall under a single category can be incorporated in the patch. For instance, the patch can include multiple analgesics, such as acetaminophen with codeine, acetaminophen with hydrocodone (vicodin), and so forth. Examples of analgesics and/or NSAIDs include analgesics available over the counter (OTC) at relatively low dosages including acetamide (acetaminophen or paracetamol), acetylsalicylic acid (aspirin), ibuprofen, ketoprofen, naproxen and naproxen sodium, and so forth. Prescription analgesics and/or anti-inflammatories can include, without limitation, OTC analgesics at concentrations requiring a prescription, celecoxib, sulindac, oxaprozin, salsalate, piroxicam, indomethacin, etodolac, meloxicam, nabumetone, keteroloc and ketorolac tromethamine, tolmetin, diclofenac, diproqualone, and diflunisal. Narcotic analgesics can include codeine, hydrocodone, oxycodone, fentanyl, and propoxyphene.

DMARDs can encompass both small molecule drugs and biological agents. DMARDs may be chemically synthesized or may be produced through genetic engineering processes (e.g., recombinant techniques). Chemically synthesized DMARDs encompassed herein include, without limitation, azathioprine, cyclosporine (ciclosporin, cyclosporine A), D-penicillamine, gold salts (e.g., auranofin, Na-aurothiomalate (Myocrism), chloroquine, hydroxychloroquine, leflunomide, methotrexate, minocycline, sulphasalazine (sulfasalazine), and cyclophosphamide. Biological DMARDs include, without limitation, TNF-α blockers such as etanercept (Enbrel®), infliximab (Remicade®), adalimumab (Humira®), certolizamab pego (Cimzia®) and golumumab (Simponi™); IL-1 blockers such as anakinra (Kineret®); monoclonal antibodies against B cells including rituximab (Rituxan®); T cell costimulation blockers such as abatacept (Orencia®), and IL-6 blockers such as tocilizumab (RoActemra®, Actemra®); a calcineurin inhibitor such as tacrolimus (Prograf®). The patch may also incorporate multiple RA drugs. For instance, the patch can include a combination of DMARDs in addition to an analgesic and/or an anti-inflammatory drug. Common combinations of DMARDs include, for example, methotrexate in combination with hydroxychloroquine, methotrexate in combination with sulfasalazine, sulfasalazine in combination with hydroxychloroquine, and all three of these DMARDs together, i.e., hydroxychloroquine, methotrexate, and sulfasalazine.

If desired, the patch may employ a plurality of reservoirs for storing multiple materials for delivery. The reservoirs may be positioned adjacent to each other, either in a vertical or horizontal relationship. For instance, a first reservoir may contain a drug compound and a second reservoir may contain an excipient (e.g., delivery vehicle, such as alcohols, water, etc.; buffering agents; and so forth). In one particular embodiment, for example, the first reservoir may contain a lyophilized powder of the drug compound (e.g., RA drug) and the second reservoir may contain an aqueous solution for reconstituting the powder. Alternatively, multiple reservoirs may be employed that each contains a drug compound. Regardless, the different materials may be mixed prior to delivery.

B. Rate Control Membrane

The drug delivery assembly also contains a rate control membrane that is in fluid communication with the drug reservoir. The rate control membrane can help slow down the flow rate of the drug compound upon its release. Specifically, fluidic drug compounds passing from the drug reservoir to the microneedle assembly may experience a drop in pressure that results in a reduction in flow rate. If this difference is too great, some backpressure may be created that can impede the flow of the compound and potentially overcome the capillary pressure of the fluid through the microfluidic channels. Thus, the use of the rate control membrane can ameliorate this difference in pressure and allow the drug compound to be introduced into the microneedle at a more controlled flow rate. The particular materials, thickness, etc. of the rate control membrane can vary based on multiple factors, such as the viscosity of the drug compound, the desired delivery time, etc.

The rate-controlling membrane may be fabricated from permeable, semi-permeable or microporous materials that are known in the art to control the rate of drug compounds and having a permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

C. Other Layers

If desired, the drug delivery assembly may contain additional layers or materials that provide various benefits to the resulting transdermal patch. In one embodiment, for example, the assembly includes an adhesive layer that can help facilitate the attachment of the patch to a user's skin during use. Although not required, the adhesive layer is often disposed over the reservoir. The adhesive layer typically employs an adhesive coated onto a backing material. The backing may be made of a material that is substantially impermeable to the drug compound, such as polymers, metal foils, etc. Suitable polymers may include, for instance, polyethylene terephthalate, polyvinylchloride, polyethylene, polypropylene, polycarbonate, polyester, and so forth. The adhesive may be a pressure-sensitive adhesive as is known in the art. Suitable adhesives may include, for instance, solvent-based acrylic adhesives, solvent-based rubber adhesives, silicone adhesives, etc.

II. Microneedle Assembly

The transdermal patch of the present invention also contains a microneedle assembly that is capable of being placed in fluid communication with the drug delivery assembly described above. The microneedle assembly contains a plurality of microneedles that extend outwardly from a support. Referring to FIGS. 13-14, for example, one particular embodiment of a microneedle assembly 310 is shown in more detail that contains a plurality of microneedles 318 that extend from a support 312. The support 312 may be constructed from a rigid or flexible sheet of metal, ceramic, plastic or other material. The support 312 can vary in thickness to meet the needs of the transdermal patch, such as about 1000 micrometers or less, in some embodiments from about 1 to about 500 micrometers, and in some embodiments, from about 10 to about 200 micrometers. Regardless of the manner in which it is constructed, an aperture 328 may be formed in the support 312 that extends through a first surface 314 and a second opposing surface 316. In the embodiment depicted in FIGS. 13 and 14, the microneedles 318 extend from the second surface 316, although in other embodiments the microneedles 318 may extend from the first surface 314 or elsewhere.

Figure 17:
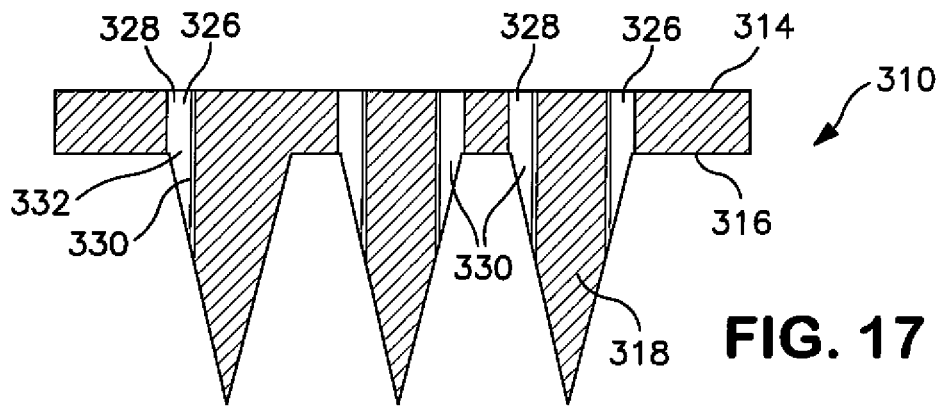
FIGS. 17 and 18 are partial cross-sectional views of microneedle assemblies that may be formed in accordance with an embodiment of the present invention.
Figure 18:
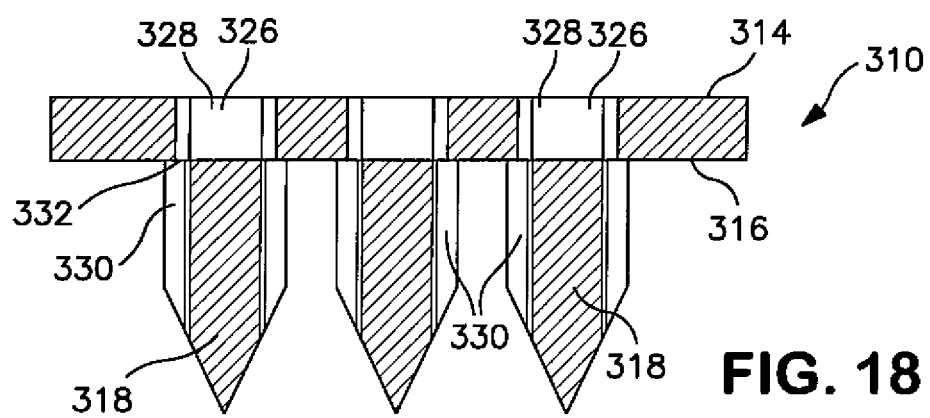

It should be understood that the number of microneedles 318 shown in the figures is for illustrative purposes only. The actual number of microneedles used in the patch may, for example, range from about 500 to about 10,000, in some embodiments from about 2,000 to about 8,000, and in some embodiments, from about 4,000 to about 6,000. The size and shape of the microneedles 318 may also vary as desired. For example, the microneedles 318 of FIGS. 13 and 14 have an overall conical shape. In alternative embodiments, however, the microneedles 318 may have an overall pyramidal shape or a cylindrical portion upon which is positioned a conical portion having a tip, such as is shown in FIGS. 17-18. Regardless, the microneedle 318 typically includes a base 320 and a tip 322. As shown in FIG. 13, the base 320 is the portion of the microneedle 318 that is proximate to the second surface 316 of the support 312. The tip 322 of the microneedle 318 is the point of the microneedle 318 that is furthest from the base 320. Although the tip 322 may be variously formed, it typically has a radius that is less than or equal to about 1 micrometer. The microneedles 318 are typically of a length sufficient to penetrate the stratum corneum and pass into the epidermis, but not penetrate through the epidermis and into the dermis in applications where it is desirable to minimize pain. In certain embodiments, the microneedles have a length (from their tip 322 to their base 320) of about 500 micrometers or less, in some embodiments from 1 to about 400 micrometers, and in some embodiments, from about 50 to about 350 micrometers.

The microneedles 318 may be arranged on the substrate in a variety of patterns, and such patterns may be designed for a particular use. For example, the microneedles may be spaced apart in a uniform manner, such as in a rectangular or square grid or in concentric circles. The spacing may depend on numerous factors, including height and width of the microneedles 318, as well as the amount and type of substance that is intended to be moved through the microneedles. While a variety of arrangements of microneedles is useful in the present invention, a particularly useful arrangement of microneedles 318 is a "tip-to-tip" spacing between microneedles of about 50 micrometers or more, in some embodiments about 100 to about 800 micrometers, and in some embodiments, from about 200 to about 600 micrometers. The microneedles 318 may be formed of various substances such as, for example, polymers, ceramics and metals. While numerous processes may be used to manufacture microneedles according to the present invention, a suitable production system is MEMS (Micro-Electro-Mechanical Systems) technology and microfabrication processes. MEMS is capable of forming micromechanical and other elements such as semiconductors on a single silicon substrate using microfabrication processes such as etching, micromachining or other processes. The support 312 may be manufactured from silicon, the microneedles being subsequently formed by a microetching process. Micromolding techniques may also be used to form the microneedles 318 and support 312.

Regardless of their particular configuration, the microneedles generally define at least one channel that is in fluidic communication with at least a portion of the aperture of the support. The dimensions of the channel are specifically selected in the present invention to induce capillary flow of the drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio is determined from the average dimensions.

Referring again to FIGS. 13-14, for example, the illustrated microneedles 318 contain at least one channel 330. The channel may be located in a variety of different positions, such as in the interior of the channel, on an exterior surface, etc. In the embodiment illustrated in FIGS. 13-14, for example, the channel 330 is located on an exterior surface 324 of the microneedle 318. The cross-section of the channel 330, as shown in FIGS. 15-16, is substantially U-shaped. The channel 330 may also be arcuate or have any other configuration suitable for moving a substance therethrough, such as, for example, V-shaped or C-shaped. Regardless, a pathway 326 is formed by the channel 330 and the aperture 328, which meet at a junction 332 that is generally located in the plane of the second surface 316. Each microneedle 318 may deliver or extract drug compounds through the skin via the pathway 326, as depicted in FIG. 14. The pathway 326 enables the compound to flow from the first surface 314 through the aperture 328, the junction 332 and exiting into the channel 330. By enabling the compound to flow through the support 312 and directly into the channel 330, more precise control over the delivery location and the amount of substance delivered may be provided.

In certain embodiments and as shown in FIG. 17, an aperture 328 is aligned with a single channel 330 via a junction 332. Alternately and as shown in other figures, a single aperture may feed two or more separate channels 330.

Figure 19:
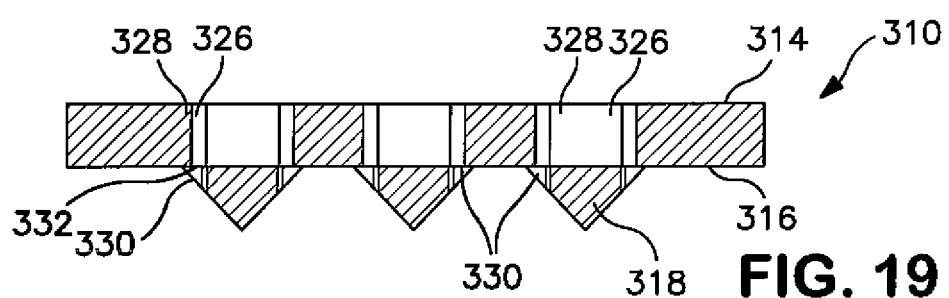
FIG. 19 is a cross-sectional view of a microneedle assembly in accordance with an embodiment of the present invention.

The channel 330 may extend from the junction 332 at the base 320 of the microneedle to the tip 322, as depicted in FIGS. 13 and 14. In other embodiments, the channel 330 may not extend the full length of the microneedle 318 to the tip 322. Each microneedle 318 may include more than one channel 330, as seen in the embodiments of FIGS. 17-19. Alternate embodiments may include more channels if desired. The channel 330 may be variously positioned on the exterior surface 324, forming a substantially linear path from the base 320 towards the tip 322, or forming a winding or circuitous path along the exterior surface 324. In microneedles where two or more channels are present, the channels 330 may be variously spaced around the microneedle 318 in a symmetrical or asymmetrical manner.

FIG. 16 is a view looking at the first surface 314 of the microneedle assembly 310, which shows the junction 332 that is formed in the pathway 326 by the overlapping portions of the aperture 328 and the channel 330. FIG. 15 is a view looking down onto the second surface 316 of the microneedle 318, showing the junction 332 as seen from that portion of the microneedle assembly 310, which may be in contact with the skin of a user. The junction 332 may vary in area between pathways 326 on a given microneedle 318, and may vary between microneedles 318 on a given microneedle assembly 310. The area of the junction 332 may vary widely, and will depend on factors such as, for example, the diameter of the microneedle 318, the viscosity of the substance to be moved through the pathway 326 and the quantity of substance to be delivered. In certain embodiments, the area of the junction 332 at the second surface 316 is greater than or equal to about 100 square microns, although smaller areas may also be acceptable for use in the present invention. In other embodiments, the area of the junction 332 at the second surface 316 may be equal to about 150 square microns or greater.

Figure 20:
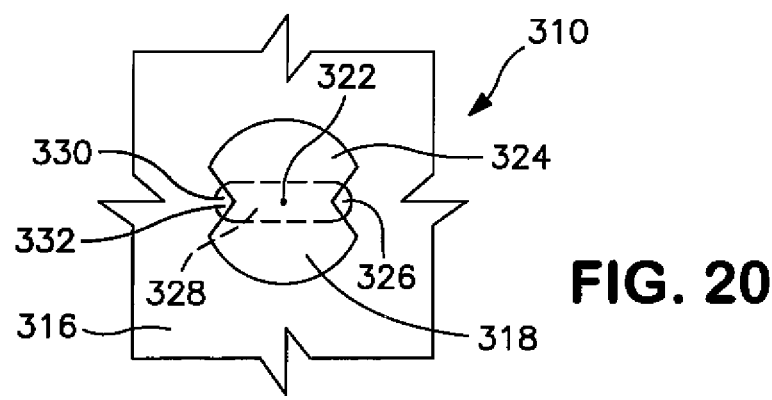
FIG. 20 is a top view of another microneedle assembly that may be formed in accordance with an embodiment of the present invention.

FIG. 17 illustrates embodiments of the microneedle 318 in which the aperture 328 and channel 330 have sides that are not only coextensive with each other but may also be planar for at least some distance along the length of the pathway 326. FIGS. 18-19 illustrate an embodiment where a single aperture 328 is aligned with more than one channel 330 on a particular microneedle 318. FIG. 20 is a view of the second surface 316 of the microneedle assembly 310 shown in FIG. 19, illustrating the alignment of the microneedle 318, the channels 330, the aperture 328 and the junctions 332.

III. Release Member

As indicated above, a release member is initially positioned adjacent to the microneedle assembly and the drug delivery assembly so that it is adjacent to the support of the microneedle assembly and the rate control membrane of the drug delivery assembly. It should be understood, however, that the release layer need not contact such layers, and that other layers may be in fact be positioned between the release member and the support and/or rate control membrane. Regardless, the release member is made of a material that is substantially impermeable to the drug compound, such as a polymeric material, metal, etc. The material is also desirably hydrophobic. Suitable polymeric materials may include, for instance, polyethylene terephthalate, polyvinylchloride, polyethylene, polypropylene, polycarbonate, polyester, metal foils, and so forth. Because it is generally impermeable, the release member can initially seal the aperture in the support and thus limit the flow of the drug compound therethrough. When it is desired to use the patch, a force may be applied by the user to at least partially separate the release member, thereby breaking the seal.

The separation of the release member may be accomplished in a variety of ways. For instance, a portion of the release member may simply be ruptured. Any of a variety of known techniques for forming a rupturable layer may be employed in the present invention. In one embodiment, for example, the release member may be bonded about its perimeter. The strength of the bonds may exceed the tensile strength of the release member so that when a tensile force is applied, an inner portion of the substrate ruptures while the bonded perimeter remains in tact.

Figure 2:
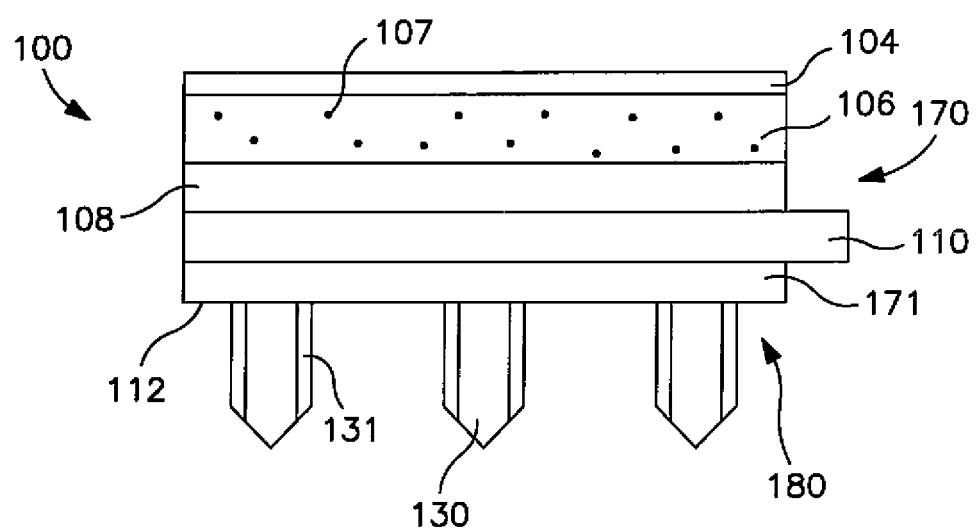
FIG. 2 is a front view of the patch of FIG. 1.

In alternative embodiments, separation may be accomplished through the partial or complete detachment of the release member. For example, referring to FIGS. 1-6, one embodiment of a release member is shown that is configured to be detached from the transdermal patch to initiate the flow of the drug compound. More particularly, FIGS. 1-2 show a transdermal patch 100 that contains a drug delivery assembly 170 and a microneedle assembly 180. The drug delivery assembly 170 includes a reservoir 106 positioned adjacent to a rate control membrane 108, such as described above. Although optional, the assembly 170 also contains an adhesive layer 104 that is positioned adjacent to the reservoir 106. The microneedle assembly 180 likewise includes a support 112 from which extends a plurality of microneedles 130 having channels 131, such as described above. The layers of the drug delivery assembly 170 and/or the microneedle assembly 180 may be attached together if desired using any known bonding technique, such as through adhesive bonding, thermal bonding, ultrasonic bonding, etc.

Figure 3:
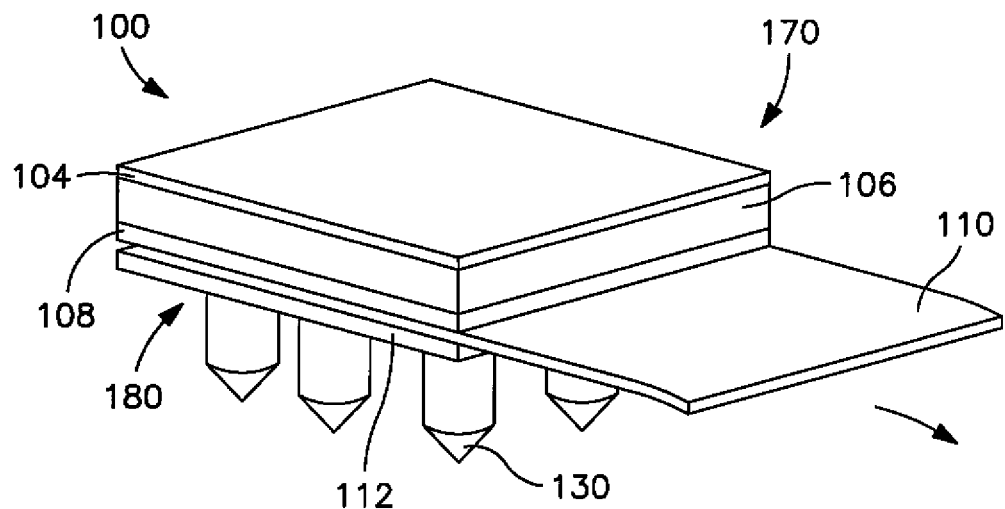
FIG. 3 is a perspective view of the patch of FIG. 1 in which the release member is partially withdrawn from the patch.
Figure 4:
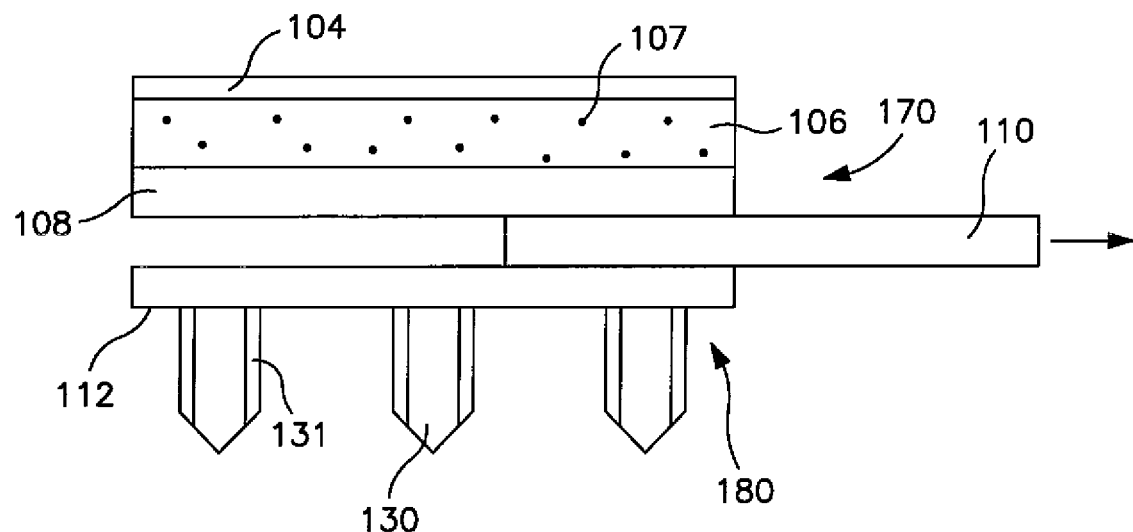
FIG. 4 is a front view of the patch of FIG. 3.
Figure 5:
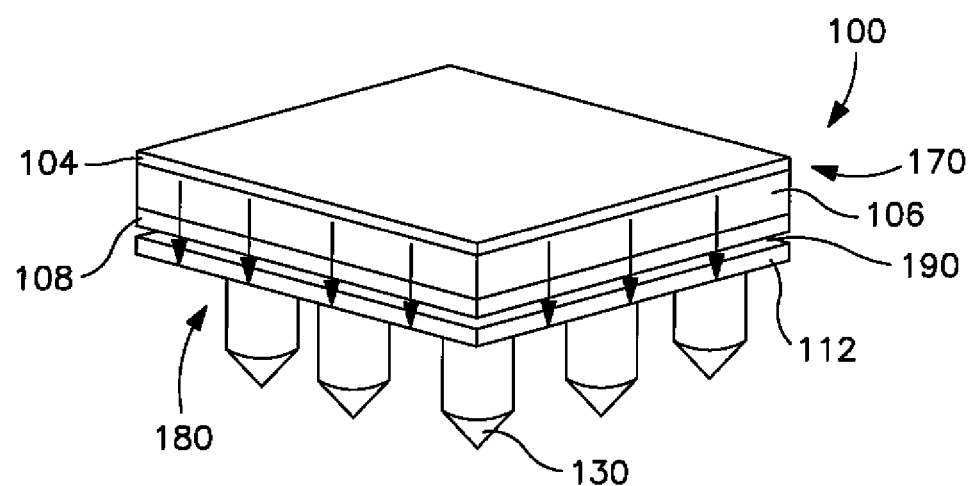
FIG. 5 is a perspective view of the transdermal patch of FIG. 1 after removal of the release member and during use.
Figure 6:
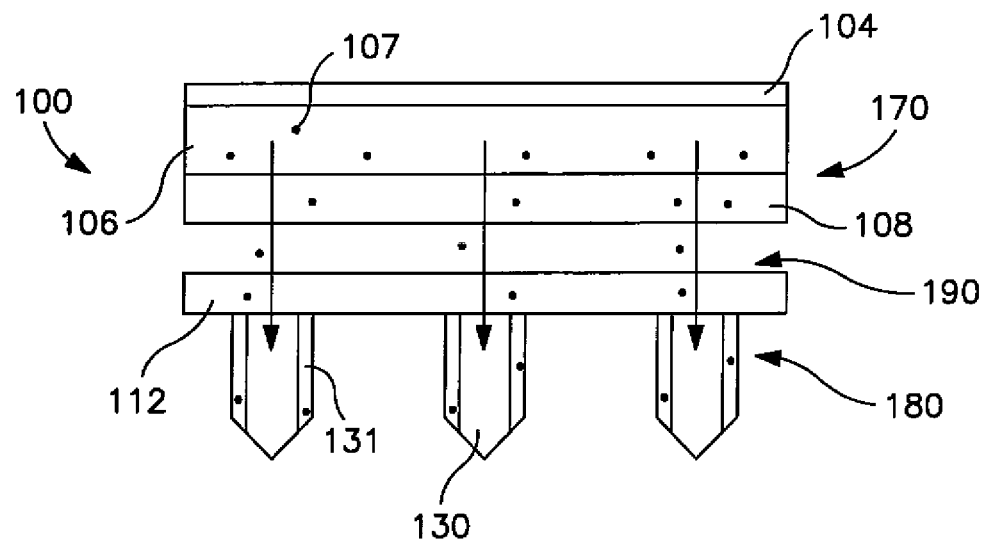
FIG. 6 is a front view of the patch of FIG. 5.

Regardless of the particular configuration employed, the patch 100 also contains a release member 110 that is positioned between the drug delivery assembly 170 and the microneedle assembly 180. While the release member 110 may optionally be bonded to the adjacent support 112 and/or rate control membrane 108, it is typically desired that it is only lightly bonded, if at all, so that the release member 110 can be easily withdrawn from the patch 100. If desired, the release member 110 may also contain a tab portion 171 (FIGS. 1-2) that extends at least partly beyond the perimeter of the patch 100 to facilitate the ability of a user to grab onto the member and pull it in the desired direction. In its "inactive" configuration as shown in FIGS. 1-2, the drug delivery assembly 170 of the patch 100 securely retains a drug compound 107 so that it does not flow to any significant extent into the microneedles 130. As indicated above, the patch can be "activated" by simply applying a force to the release member so that it is detached from the patch. Referring to FIGS. 3-4, one embodiment for activating the patch 100 is shown in which the release member 110 is pulled in a longitudinal direction. The entire release member 110 may be removed as shown in FIGS. 5-6, or it may simply be partially detached as shown in FIGS. 3-4. In either case, however, the seal previously formed between the release member 110 and the aperture (not shown) of the support 112 is broken. In this manner, a drug compound 107 can begin to flow from the drug delivery assembly 170 and into the channels 131 of the microneedles 130 via the support 112. An exemplary illustration of how the drug compound 107 flows from the reservoir 106 and into the channels 131 is shown in FIGS. 5-6. Notably, the flow of the drug compound 107 is passively initiated and does not require any active displacement mechanisms (e.g., pumps).

In the embodiments shown in FIGS. 1-6 and discussed above, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 7:
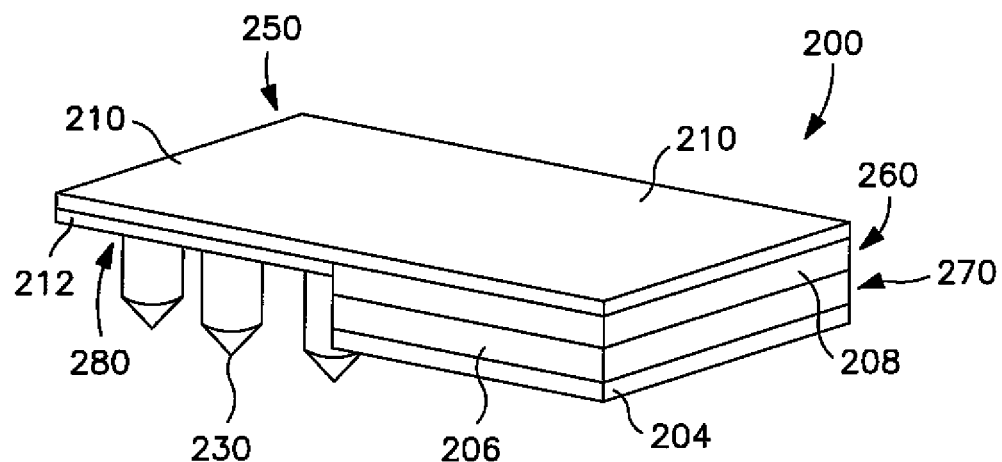
FIG. 7 is a perspective view of another embodiment of a transdermal patch of the present invention prior to delivery of a drug compound.
Figure 8:
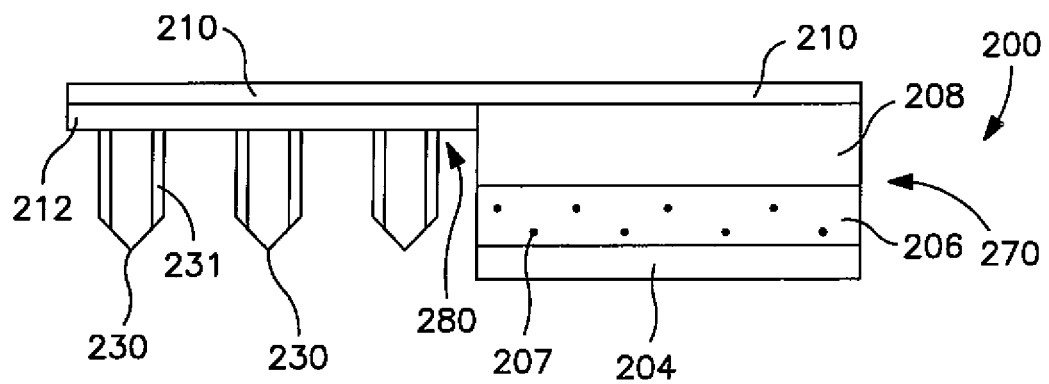
FIG. 8 is a front view of the patch of FIG. 7.

Referring to FIGS. 7-12, for example, one particular embodiment of a patch 200 is shown. FIGS. 7-8 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

Figure 9:
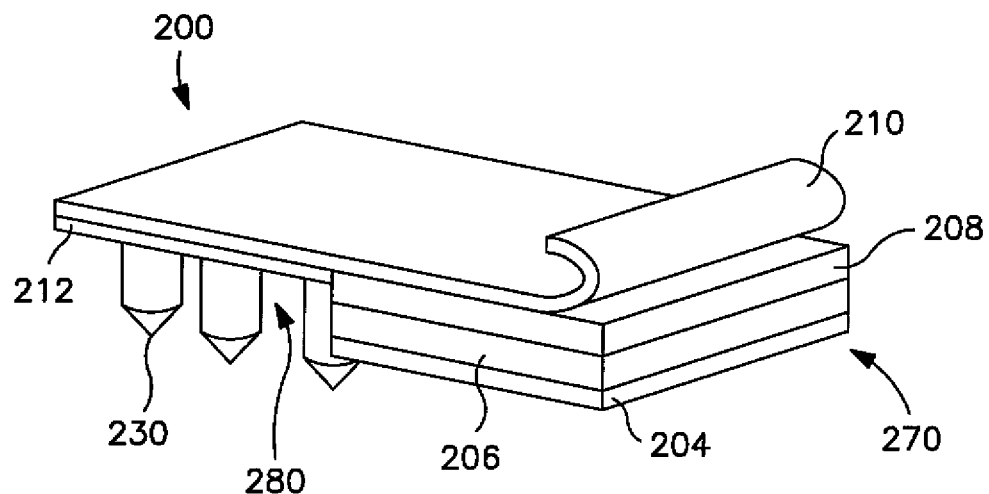
FIG. 9 is a perspective view of the patch of FIG. 7 in which the release member is partially peeled away from the patch.
Figure 10:
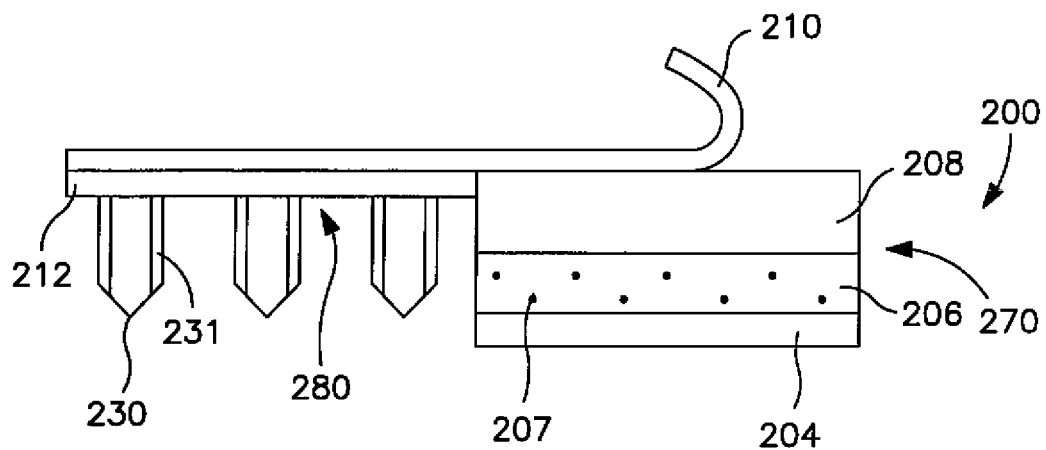
FIG. 10 is a front view of the patch of FIG. 9.
Figure 11:
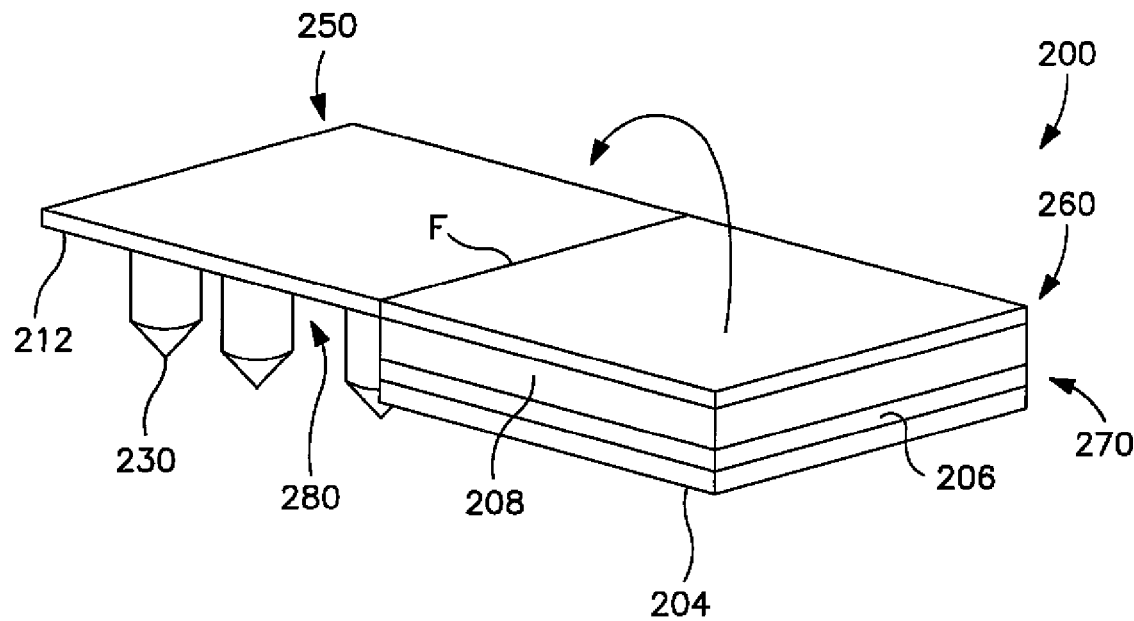
FIG. 11 is a perspective view of the patch of FIG. 7 in which the release member is completely peeled away from the patch.
Figure 12:
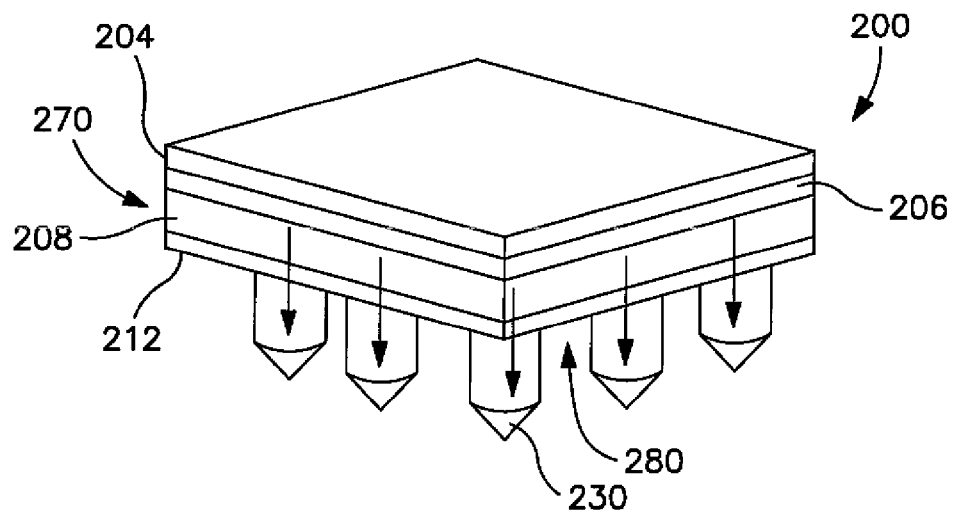
FIG. 12 is a perspective view of the transdermal patch of FIG. 7 after removal of the release member and during use.

In this embodiment, the support 212 and the rate control membrane 208 are initially positioned horizontally adjacent to each other, and a release member 210 extends over the support 212 and the rate control member 208. In this particular embodiment, it is generally desired that the release member 210 releasably attached to the support 212 and the rate control membrane 208 with an adhesive (e.g., pressure-sensitive adhesive). In its "inactive" configuration as shown in FIGS. 7-8, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 9-10, to break the seal previously formed between the release member 210 and the aperture (not shown) of the support 212. Thereafter, the second section 260 may be folded about a fold line "F" as shown by the directional arrow in FIG. 11 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 12).

Figure 21:
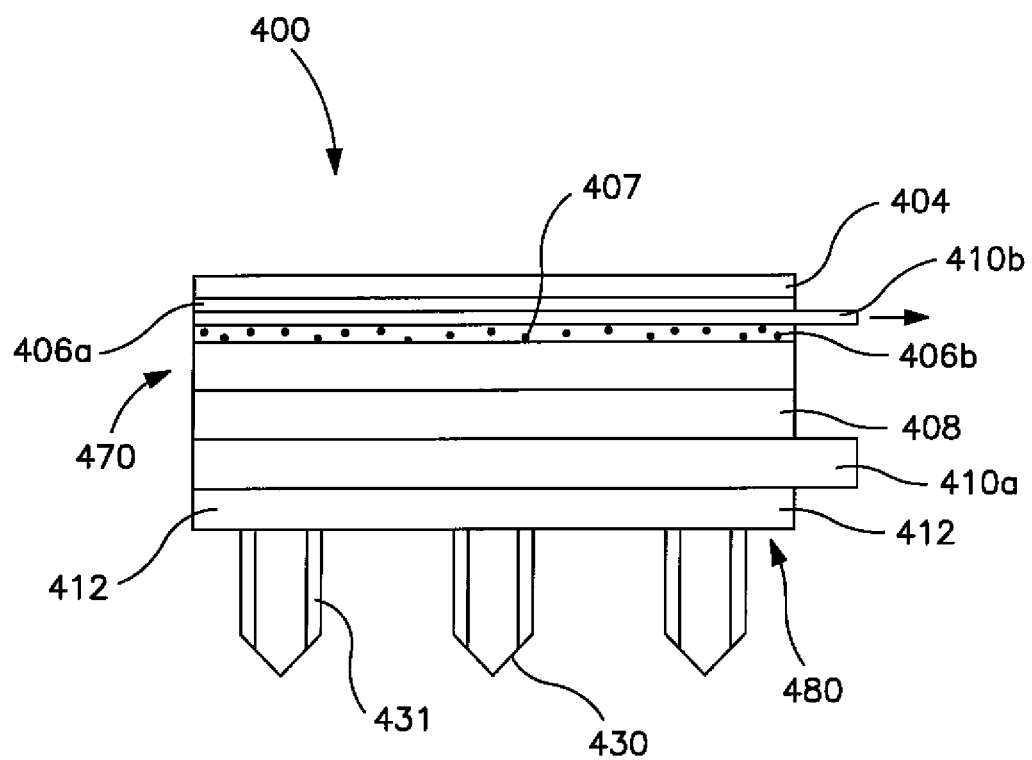
FIG. 21 is a perspective view of yet another embodiment of a transdermal patch of the present invention prior to delivery of a drug compound.

The embodiments illustrated above contain only a single release member. However, it should be understood that additional release members may be employed in the present invention to accomplish a variety of different purposes. Referring to FIG. 21, for example, one particular embodiment of a patch 400 is shown that employs a drug delivery assembly 470 and a microneedle assembly 480. In this embodiment, the drug delivery assembly 470 includes two separate reservoirs 406*a* and 406*b*, respectively, such as described above. The second reservoir 406*b* may, for example, contain a powdered drug compound 407 (e.g., RA drug) and the first reservoir 406*a* may contain a liquid solution (not shown) for reconstituting the powder. Initially, the solution and drug compound remain separate to enhance the long term stability of the drug compound. Prior to use, however, a first release member 410*b* may be separated from the reservoirs 406*a* and 406*b* by any of the techniques mentioned above, such as by rupturing it or pulling it in the direction of the arrow shown in FIG. 21. In any event, separation of the first release member 410*b* causes the ingredients in the reservoirs to mix together to form a solution form of the drug compound. Thereafter, a second release member 410*a* may likewise be separated from a rate control membrane 408 and a support 412 of the microneedle assembly 480. This causes the drug compound to flow from the rate control membrane 408 into channels 431 of the microneedles 430. Although optional, the patch 400 may also contain an adhesive layer 404 to help adhere it to the skin of a user.

Regardless of the particular manner in which it is employed, the present inventors have discovered that the release member can provide a variety of different benefits to the resulting transdermal patch. For instance, because the release member is easily separated, flow of the drug compound may be initiated by a user without necessarily requiring the aid of a medical professional. Furthermore, because it is configured for separation, the extent to which the release member is bonded to adjacent layers is generally minimized, if at all. Such a lightly bonded release member may leave a small space between the layers to which it is adjacent when it is separated (partially or completely) therefrom. Notably, the present inventors have discovered that this small space may form a microreservoir that temporarily holds the drug compound before it enters the microneedle assembly. Among other things, this microreservoir is believed to further assist in the capillary flow through the channels of the microneedles. Just as an example, one embodiment of such a microreservoir is shown in more detail in FIGS. 5-6 as element 190. Although it may vary, the thickness of the microreservoir 190 is typically from about 50 nanometers to about 50 micrometers, in some embodiments from about 100 nanometers to about 10 micrometers, and in some embodiments, from about 200 nanometers to about 1 micrometer.

While the invention has been described in detail with respect to the specific embodiments thereof, it will be appreciated that those skilled in the art, upon attaining an understanding of the foregoing, may readily conceive of alterations to, variations of, and equivalents to these embodiments. In addition, it should be noted that any given range presented herein is intended to include any and all lesser included ranges. For example, a range of from 45-90 would also include 50-90; 45-80; 46-89 and so forth. Accordingly, the scope of the present invention should be assessed as that of the appended claims and any equivalents thereto.

What is claimed is:

1. A transdermal patch comprising:
a drug delivery assembly that comprises a reservoir for holding a drug compound and a rate control membrane that is in fluid communication with the reservoir;
a microneedle assembly that comprises a support having a first surface and a second surface, wherein an aperture extends between the first surface of the support and the second surface of the support, and wherein the microneedle assembly further comprises a plurality of microneedles that extend outwardly from the second surface of the support, wherein at least one of the microneedles contains a channel that is in fluid communication with the aperture and has a cross-sectional dimension ranging from about 1 micrometer to about 100 micrometers; and
a release member that is generally impermeable to the drug compound and positioned adjacent to the rate control membrane of the drug delivery assembly and the first surface of the support of the microneedle assembly, wherein the release member is configured to be at least partially separated from the rate control membrane of the drug delivery assembly and the support of the microneedle assembly when the patch is an active configuration, wherein the release member is positioned between the rate control membrane and the support.

2. The transdermal patch of claim 1, wherein the drug compound has a molecular weight of from about 20 kDa to about 250 kDa.

3. The transdermal patch of claim 1, wherein the drug compound is a rheumatoid arthritis drug compound.

4. The transdermal patch of claim 3, wherein the drug compound is a TNF-α blacker.

5. The transdermal patch of claim 1, wherein the drug delivery assembly further comprises an adhesive layer, the reservoir being positioned between the adhesive layer and the rate control membrane.

6. The transdermal patch of claim 1, wherein the cross-sectional dimension of the channel is from about 5 micrometers to about 50 micrometers.

7. The transdermal patch of claim 1, wherein an aspect ratio of the channel is from about 5 to about 40.

8. The transdermal patch of claim 1, wherein a length of the channel is from about 50 micrometers to about 500 micrometers.

9. The transdermal patch of claim 1, wherein a cross-sectional area of the channel is from about 100 square micrometers to about 500 square micrometers.

10. The transdermal patch of claim 1, wherein the microneedles contain a base that extends from the second surface of the support and a tip that extends from the base.

11. The transdermal patch of claim 10, wherein the channel is disposed on an exterior surface of the base.

12. The transdermal patch of claim 10, wherein the channel is in alignment with at least a portion of the aperture to form a junction through which the drug compound is able to pass, the junction being formed in a plane of the second surface at the base of the microneedle.

13. The transdermal patch of claim 10, wherein the channel forms a substantially linear path from the base to the tip.

14. The transdermal patch of claim 1, wherein the support defines a plurality of apertures, wherein at least a portion of one of the apertures is in alignment with the channel.

15. The transdermal patch of claim 1, wherein the release member contains a tab portion that extends at least partially beyond a perimeter of the patch.

16. The transdermal patch of claim 1, wherein the release member is configured to be detached from the patch to place the drug delivery assembly in fluid communication with the microneedle assembly.

17. The transdermal patch of claim 1, wherein a microreservoir is formed between the rate control membrane and the support upon separation of the release member.

* * * * *